US009204978B2

(12) United States Patent
Steiner et al.

(10) Patent No.: US 9,204,978 B2

(45) Date of Patent: Dec. 8, 2015

(54) MODULAR SCREW APPARATUS AND METHOD

(75) Inventors: Andrew J. Steiner, Warsaw, IN (US); Walter W. Thomas, Warsaw, IN (US); Christopher J. Holt, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 799 days.

(21) Appl. No.: 13/482,445

(22) Filed: May 29, 2012

(65) Prior Publication Data

US 2013/0325139 A1 Dec. 5, 2013

(51) Int. Cl.

| | |
|---|---|
| ***A61F 2/46*** | (2006.01) |
| *A61B 17/17* | (2006.01) |
| *A61F 2/34* | (2006.01) |
| *A61F 2/30* | (2006.01) |

(52) U.S. Cl.

CPC ........... *A61F 2/4684* (2013.01); *A61B 17/1746* (2013.01); *A61F 2/34* (2013.01); *A61F 2002/3085* (2013.01); *A61F 2002/30367* (2013.01); *A61F 2002/30433* (2013.01); *A61F 2002/3403* (2013.01)

(58) Field of Classification Search

CPC ....... A61F 2/4684; A61F 2/34; A61F 2/4609; A61F 2002/3429; A61F 2002/3404; A61F 2002/4629; A61F 2/30721; A61B 17/1746

USPC ......................................... 623/22.28; 606/91

See application file for complete search history.

(56) References Cited

U.S. PATENT DOCUMENTS

| | | | | |
|---|---|---|---|---|
| 5,976,148 | A * | 11/1999 | Charpenet et al. | 606/91 |
| 6,152,961 | A | 11/2000 | Ostiguy, Jr. et al. | |
| 6,610,097 | B2 | 8/2003 | Serbousek et al. | |
| 7,294,150 | B1 | 11/2007 | Mandell et al. | |
| 2006/0069443 | A1* | 3/2006 | Deffenbaugh et al. | 623/19.11 |
| 2007/0250175 | A1* | 10/2007 | Meridew et al. | 623/22.21 |
| 2009/0182384 | A1* | 7/2009 | Wilcox et al. | 606/305 |
| 2009/0281579 | A1* | 11/2009 | Weaver et al. | 606/286 |

* cited by examiner

*Primary Examiner* — David Bates

*Assistant Examiner* — Samuel Hanna

(74) *Attorney, Agent, or Firm* — Schwegman Lundberg & Woessner, P.A.

(57) ABSTRACT

An orthopedic instrument comprises a shell configured to be inserted into a cup-shaped site, a liner configured to be received within a cavity of the shell, wherein the liner has an aperture and a mating feature adjacent to the aperture, and a modular screw configured to be received within the aperture of the liner. The modular screw can include a first component that is positionable adjacent to a first side of the mating feature and a second component that is positionable adjacent to a second side of the mating feature. When assembled, the modular screw can be configured to rotate relative to the liner.

12 Claims, 4 Drawing Sheets

MODULAR SCREW APPARATUS AND METHOD

BACKGROUND

A primary bone joint prosthesis can augment or replace one or more portions of a joint. Arthroplasty procedures, whether total or partial, can function to fix damaged joints as well as relieve the pain associated with arthritis. A revision joint prosthesis can augment or replace a primary bone joint prosthesis that is loose, unstable, worn, or broken.

For example, a hip arthroplasty can involve determining a proper acetabular cup size for implantation. A provisional shell size can be selected according to acetabulum geometry and bone quality. After the provisional shell is placed in the acetabulum, a provisional liner can be fastened to the provisional shell to determine a range of motion of a number of components of a hip prosthesis. The provisional shell size and provisional liner size can be used to fit an acetabular cup for the hip joint prosthesis.

U.S. Pat. No. 7,294,150 is directed to a liner member configured to be received by an acetabular cup. Particularly, the liner member and the acetabular cup are mated together via a force-fit deforming seal, so as to prevent passage of fluid.

SUMMARY

The present inventors have recognized, among other things, that a shell and liner can detach during trial reduction, in the case of a provisional liner or shell, or during implantation. In such instances, an attachment mechanism can fail due to off-axis torquing, material fatigue, improper design, or the like.

In an example, an instrument can be provided that includes a shell configured to be inserted into a cup-shaped site, a liner configured to be received within a cavity of the shell, wherein the liner has an aperture and a mating feature adjacent to the aperture, and a modular screw configured to be received within the aperture of the liner. The modular screw can include a first component that is positionable adjacent to a first side of the mating feature and a second component that is positionable adjacent to a second side of the mating feature. When assembled, the modular screw can be configured to rotate relative to the liner.

In an example, the first component of the modular screw can be a female component having a threaded portion configured to be attached to the shell. The second component of the modular screw can be a male component configured to be received within a recess in the female component so as to couple the modular screw about the mating feature.

In an example, the male component can be configured to be coupled to the female component with a press fit connection.

In an example, the male component can be configured to be coupled to the female component with a snap fit connection.

In an example, the male component can be fused to the female component to prevent separation of the male and female components.

In an example, the male component and the female component can be fused together using electron beam welding.

In an example, the male component includes can include a head having a cavity configured to receive a torque driver for attaching the modular screw to the shell.

In an example, the cavity can include a depth configured to permit a threshold torque for attaching the threaded portion of the female component to the shell.

In an example, the mating feature can be a radially extending flange.

In an example, the radially extending flange can be configured to withstand off-axis leveraging of the modular screw.

In an example, the female component can include a female seating surface configured to be positioned adjacent to the first side of the radially extending flange.

In an example, the head of the male component can include a male seating surface configured to be positioned adjacent to the second side of the radially extending flange.

In an example, the instrument can include a lateral motion deterrent, wherein the second side of the radially extending flange can include a groove configured to receive a protrusion extending from the male seating surface to prevent lateral movement of the modular screw relative to the liner.

In an example, a lateral dimension of the radially extending flange can be greater than a lateral dimension of the seating surfaces of the female and male components.

In an example, the first component of the modular screw can include a first flange configured to be positioned adjacent to the first side of the mating feature. The second component can include a second flange configured to be positioned adjacent to the second side of the mating feature.

In an example, a method can include providing or obtaining a modular screw component assembled about a mating feature of a liner component, wherein the modular screw is captured by the mating feature and is configured to rotate about the mating feature. The liner component can be inserted into a cavity of a shell component and the modular screw can be attached to the shell component.

In an example, the modular screw the male component can be press or snap fitted into the female component.

In an example, the male and female components can be electron beam welded together.

In an example, a trial reduction can be conducted. The trial reduction can include assessing stability of the shell component within a cup-shaped site and assessing range of motion of one or more components coupled to the shell component or the liner component.

In an example, an instrument can be provided that includes a liner configured to be received within a cavity of the shell, the liner having an aperture and a mating feature adjacent to the aperture. A modular screw can be configured to be received within the aperture of the liner, the modular screw can include a female component that is positionable adjacent to a first side of the mating feature and a male component that is positionable adjacent to a second side of the mating feature. The modular screw can be configured to be rotatable relative to the liner. The female component can include a threaded portion configured to be attached to the shell and the male component can be configured to be received within a recess in the female component so as to couple the modular screw about the mating feature.

This summary is intended to provide an overview of subject matter of the present patent application. It is not intended to provide an exclusive or exhaustive explanation of the invention. The detailed description is included to provide further information about the present application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present disclosure relates generally to a modular screw apparatus and method. The modular screw apparatus can include a liner configured to be received within a cavity of a shell. The liner can have an aperture and a mating feature adjacent to the aperture. A modular screw can be configured to be received within the aperture of the liner. The modular screw can include a first component positionable adjacent to a first side of the mating feature and a second component positionable adjacent to a second side of the mating feature. The modular screw can be configured to rotate relative to the liner.

Shell and liner systems can be used in primary or revision surgery in skeletally mature individuals for rehabilitating hips, shoulder, or extremities damaged as a result of noninflammatory degenerative join disease (NIDJD) or its composite diagnoses, such as osteoarthritis, avascular necrosis, traumatic arthritis, or diastrophic variant.

A cup-shaped site can be prepared such as by a reaming device that shapes the cup-shaped site according to bone quality and desired position of a bone joint prosthesis. A size of the reaming device can correspond to a provisional shell and provisional liner size. The provisional shell can be seated in the prepared cup-shaped site and readied to receive the corresponding provisional liner. A modular screw configured to extend through the provisional liner can be threaded into the provisional shell, so as to attach the provisional liner to the provisional shell. The provisional liner can include a number of anti-rotational tabs that can mate with a number of scallops of the provisional shell, so as to prevent the provisional liner from rotating within the provisional shell. One or more components can be attached to the assembled provisional shell and provisional liner to perform a trial reduction, so as to check for stability of the bone joint prosthesis, range of motion of the bone joint prosthesis, proper sizing of the shell and liner, or the like.

In an example, the modular screw can include first and second components that are affixed together such that off-axis torquing of the modular screw does not result in the modular screw disassociating from the provisional liner or the provisional shell. In such an example, the trial reduction process can better assess the potential range of motion of the bone joint prosthesis or the stability of the bone joint prosthesis due in-part to the increased fixation of the modular screw to the provisional shell or provisional liner, as compared to current shell and liner systems. Improved modular screw fixation can decrease surgery time as a result of minimizing the risk of provisional shell and provisional liner disassociation during an arthroplasty procedure.

Figure 1:
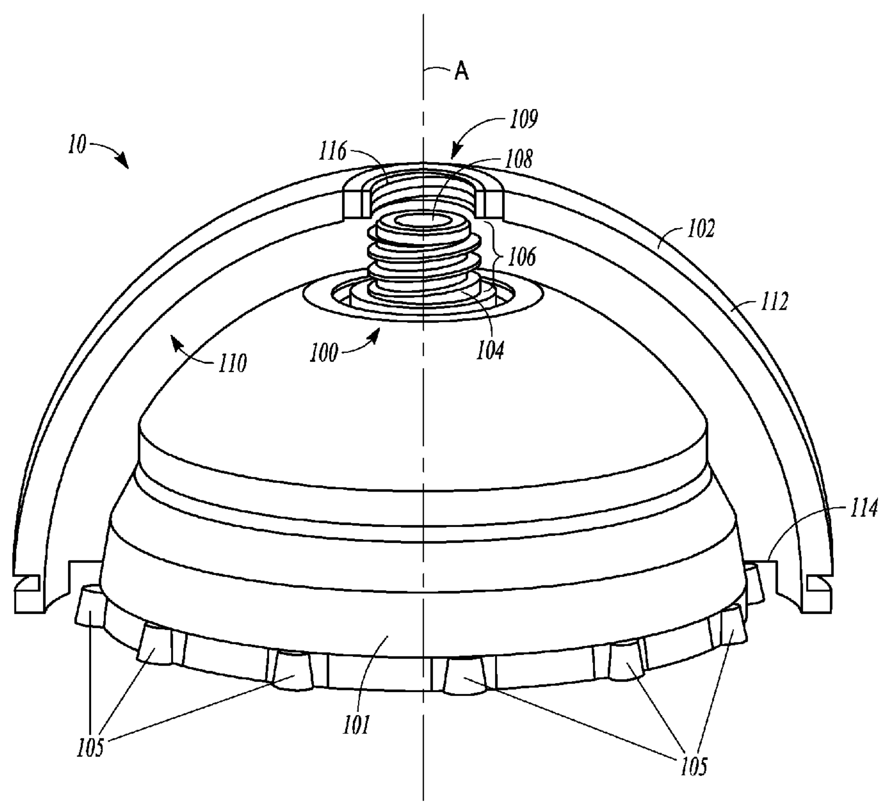
FIG. 1 is a perspective view of the modular screw apparatus assembled to the liner component and to a shell component.

FIG. 1 is a perspective view illustrating an implant instrument 10, which can include a modular screw 100, a liner 101, and a shell 102. With reference to FIG. 1, a portion of the shell 102 has been cut away to illustrate the mating relationship between the liner 101 and an internal cavity 110 of the shell 102. The liner 101 or the shell 102 can be a provisional liner or a provisional shell, such as used for temporary fixation for trial reduction purposes, as described herein. The shell 102 can have an external surface 112 that is shaped and configured to allow receipt of the shell 102 within a cup-shaped site (e.g., implant site), such as a glenoid fossa or an acetabulum, as described herein.

The implant instrument 10 can be used as a trial implant instrument, so as to aid in trial reduction, as described herein. In such an example, the modular screw 100, the liner 101, or the shell 102 can be provisional versions intended for reuse or disposal. The implant instrument 10 can be an implant designed for fixation in an implant site. In such an example, the modular screw 100, the liner 101, or the shell 102 can be designed for fixation in a subject as a bone joint prosthesis, as described herein.

The liner 101 and the shell 102 can be configured as hollow hemispherical-shaped components. The liner 101 or the shell 102 can be formed at least partially from a biocompatible material that can allow implantation of the components in a subject without eliciting an undesirable local or systemic effect in the subject. Suitable biocompatible materials can include, for example, a metallic material such as at least one of a variety of stainless steel composites, titanium, chromium-cobalt, or the like, or a non-metallic biocompatible material such as a biocompatible polymeric or other plastic material including polyamide, polyphenylsulfone, polyethersulfone, polysulfone, polyketone, polyarylamide, polyether ether ketone (PEEK), polycarbonate, polystyrene, acrylonitrile butadiene styrene (ABS), acrylics, polyetherimide, polyimide, polyphenylsulfone, polymethoylmethacrylate, fiber filled variations of these polymers, amorphous polymeric material, or various other biocompatible polymers.

The liner 101 can include one or more anti-rotational tabs 105 that can be configured for receipt within one or more scallops 114 formed within the internal cavity 110 of the shell 102. The one or more tabs 105 can be configured to mate with the one or more scallops 114 via a snap fit connection or a press fit connection. However, the one or more scallops 114 can also be sized larger than the one or more tabs 105 such that a slight amount of movement is allowed between the liner 101 and the shell 102 when the components are mated together. In an example, a series of anti-rotational tabs 105 can be disposed about a perimeter of the liner 101, such as substantially evenly spaced around the perimeter of the liner 101.

As illustrated in FIG. 1, the shell 102 can include an aperture 109 having an internally threaded portion 116 that is configured to engage an externally threaded portion 106 of the modular screw 100. Although not illustrated, the aperture 109 can engage the modular screw 100 via a non-threaded connection, such as a press fit connection, a snap fit connection, or the like. As will be discussed in further detail below, the modular screw 100 can be configured such that it is captured by the liner 101 but allowed to rotate with respect to the liner 101. Thus, the modular screw 100 can be threadably coupled to the shell 102 by rotation of the modular screw 100 relative to the liner 101.

Figure 2:
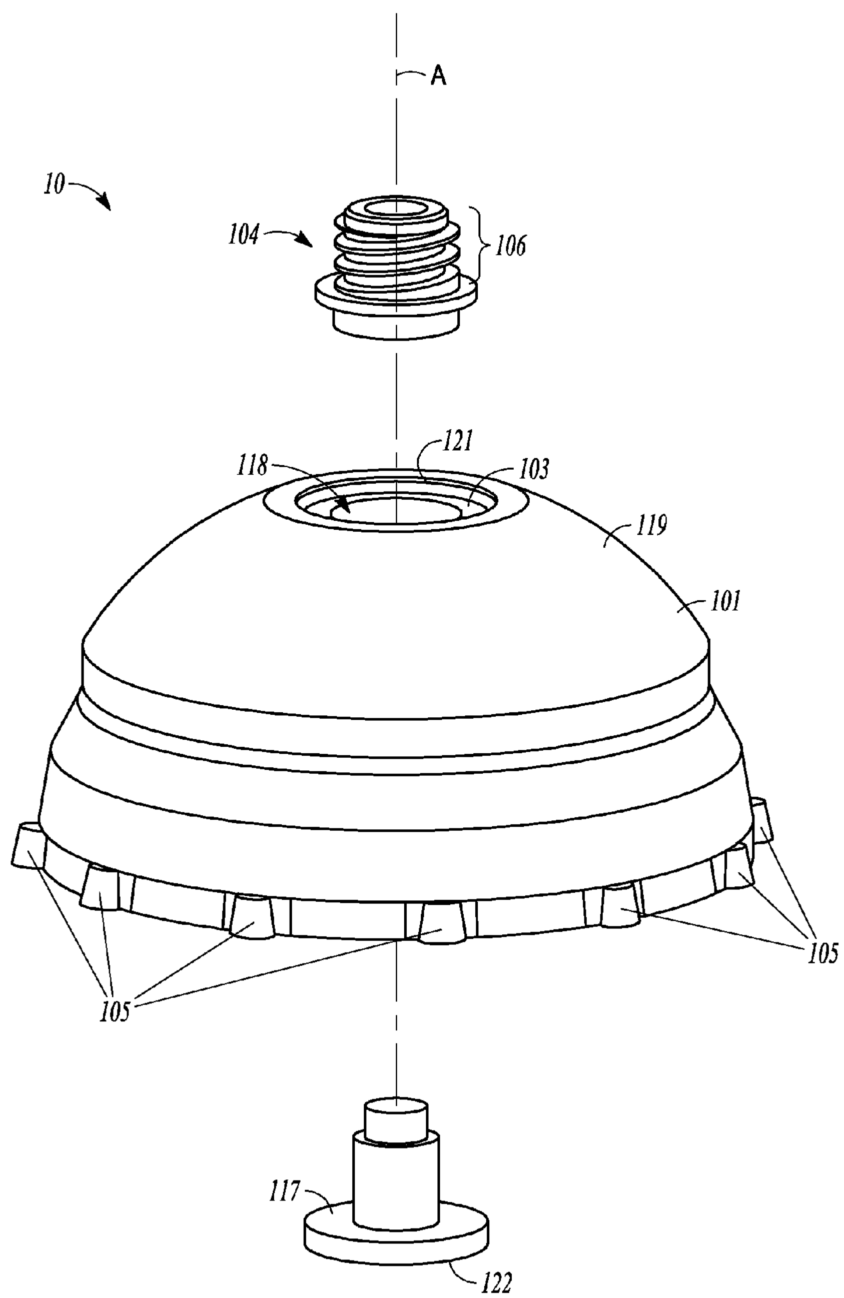
FIG. 2 is a perspective view of a modular screw apparatus disassembled from a liner component.

FIG. 2 is a perspective view of the implant instrument 10 with the shell 102 removed and the modular screw 100 disassembled from the liner 101. As illustrated in FIG. 2, the liner 101 can include an aperture 118 configured to receive a portion of the modular screw 100. The aperture 118 can be configured so as to be substantially circular, as illustrated in FIG. 2, or a number of other geometries, such as substantially rectangular, substantially triangular, or the like. The aperture 118 can be positioned substantially centered about an axis of symmetry A that is common to both the liner 101 and the shell 102, such that the aperture 118 of the liner 101 can be aligned with the aperture 109 of the shell 102 when the components are assembled as illustrated in FIG. 1.

The liner 101 can include a mating feature 103 adjacent to the aperture 118. The mating feature 103 can be formed from the same biocompatible material as the liner 101, or can alternatively be formed from a different biocompatible material. The liner 101 with the mating feature 103 can be formed as a unitary assembly, such as by injection molding. The mating feature 103 can include a radially extending flange, such as a flange that is offset from an outer surface 119 of the liner 101 and that extends radially inward from an internal wall 121 of the aperture 118 toward a center of the aperture, so as to form a smaller opening in the liner 101 than the aperture 118.

The modular screw 100 can include a first component 104 and a second component 108, as illustrated in FIG. 2. The first component 104 of the modular screw 100 can be a female component (hereinafter "female component 104") having the threaded portion 106 that can be threadably engaged with the internally threaded portion 116 of the shell as discussed above with reference to FIG. 1. The second component 108 of the modular screw 100 can be a male component (hereinafter "male component 108") configured to be received within a recess in the female component 104 so as to couple the modular screw 100 about the mating feature 103. The female component 104 or the male component 108 can be formed from a biocompatible material, as described herein. Although the first component 104 is described as the female component and the second component 108 is described as the male component, in various examples, the first component 104 can instead comprise a male component and the second component 108 can instead comprise a female component.

Figure 3:
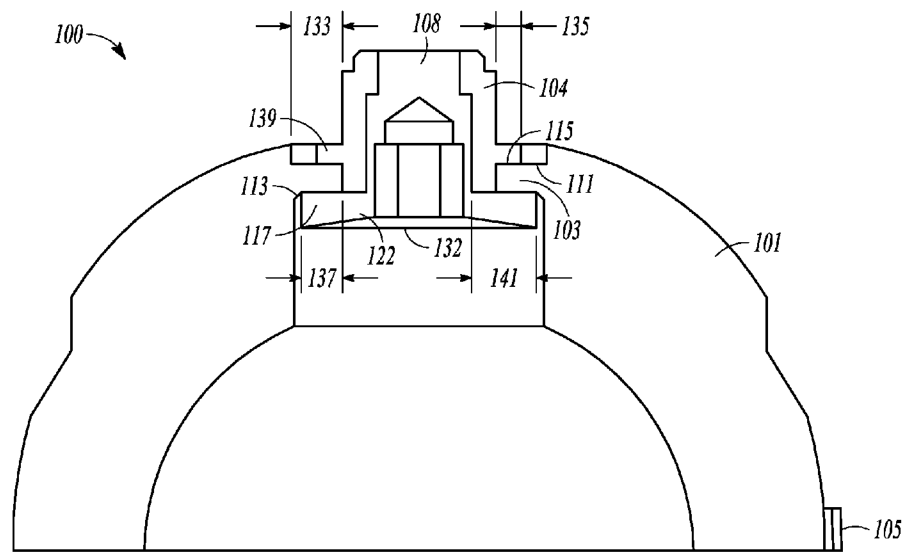
FIG. 3 is a cross-sectional view of the modular screw apparatus coupled to the liner component.

FIG. 3 is a cross-sectional view of the modular screw 100 and the liner 101. As illustrated, the female component 104 can be configured so as to be positionable adjacent to a first side 111 of the mating feature 103, which is depicted for purposes of example and not limitation as a radially extending flange 103. Particularly, the female component 104 can include a female seating surface 115 configured to be positioned adjacent to the first side 111 of the radially extending flange 103. The male component 108 of the modular screw 100 can be positionable adjacent to a second side 113 of the radially extending flange 103. Particularly, a head 122 of the male component 108 can include a male seating surface 117 configured to be positioned adjacent to the second side 113 of the radially extending flange 103.

The modular screw 100 can be configured so as to be rotatable relative to the liner 101, such that the modular screw 100 can be advanced into and threadably engage the aperture 109 of the shell 102 as the liner 101 remains substantially stationary. A lateral dimension 133 of the radially extending flange 103 can be greater than a lateral dimension 135 of the seating surface 115 of the female component 104 and a lateral dimension 137 of the seating surface 117 of the male component 108, such that the modular screw 100 can rotate relative to the liner 101. As illustrated in FIG. 3, the female seating surface 115 can be provided on a first flange 139 configured to be positioned adjacent to the first side 111 of the radially extending flange 103. In such example, the first flange 139 can define the lateral dimension 135 of the female seating surface 115. As further illustrated in FIG. 3, the male seating surface 117 can be provided on a second flange 141 configured to be positioned adjacent to the second side 113 of the radially extending flange 103. In such example, the second flange 141 can define the lateral dimension 137 of the male seating surface 117.

Figure 4:
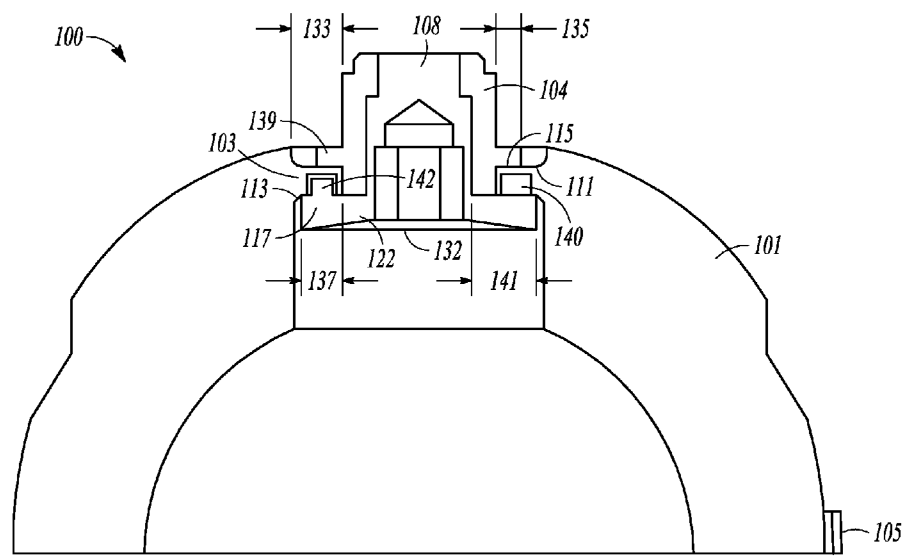
FIG. 4 is a cross-sectional view of the modular screw apparatus coupled to the liner component and illustrating a lateral motion deterrent.

FIG. 4 is a cross-sectional view of the modular screw 100 and the liner 101 illustrating a lateral motion deterrent. The lateral motion deterrent can be configured such that the second side 113 of the radially extending flange 103 can include a groove 140 configured to receive a protrusion 142 on the male seating surface 117, such that the modular screw 100 can rotate relative to the liner 101 while being guided by the protrusion 142 received within the groove 140. That is, lateral motion of the modular screw 100 can be restricted by engagement of the protrusion 142 within the groove 140, such that threading of the modular screw 100 into the aperture 109 of the shell 102 can be guided.

The male component 108 can be configured to be coupled to the female component 104 with any suitable connection, such as a press fit connection, a snap fit connection, or the like, so as to allow for secure assembly of the modular screw 100. Once assembled, the male component 108 can be fused to the female component 104, such as by electron beam welding, laser beam welding, or the like, so as to prevent separation of the male and female components. An outer surface of the male component 108 can be in contact with an inner surface of the female component 104 so that the two components can be fused together to form a solitary unit, modular screw 100.

Figure 5:
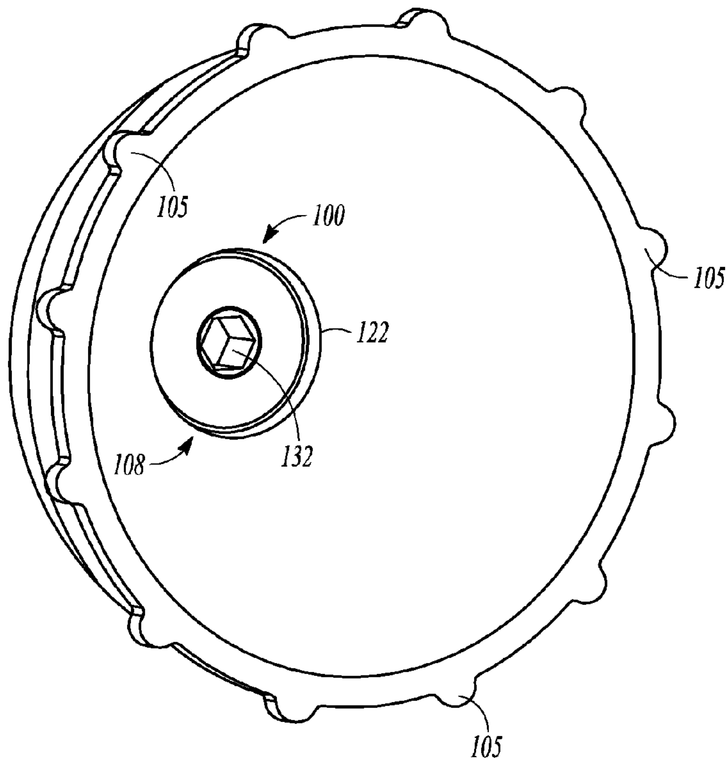
FIG. 5 is a bottom perspective view of the modular screw apparatus coupled to the liner component.

FIG. 5 is a bottom perspective view of the modular screw 100 assembled to the liner 101. As shown in FIG. 5, the head 122 of the male component 108 can include a cavity 132 configured to receive a torque driver for attaching the modular screw 100 to the shell 102. The cavity 132 can be configured to receive any suitable type of torque driver, such as a hex driver, a Phillips driver, a flathead driver, or the like. The cavity 132 can be configured so as to include a depth that can permit a threshold amount of torque for attaching the threaded portion 106 of the female component 104 to the shell 102. A threshold amount of torque can include about 11 Newton meter (Nm). The radially extending flange 103 of the liner can be configured so as to withstand off-axis leveraging of the modular screw 100, such as resulting from a trial reduction, as discussed herein in connection with FIG. 6.

Figure 6:
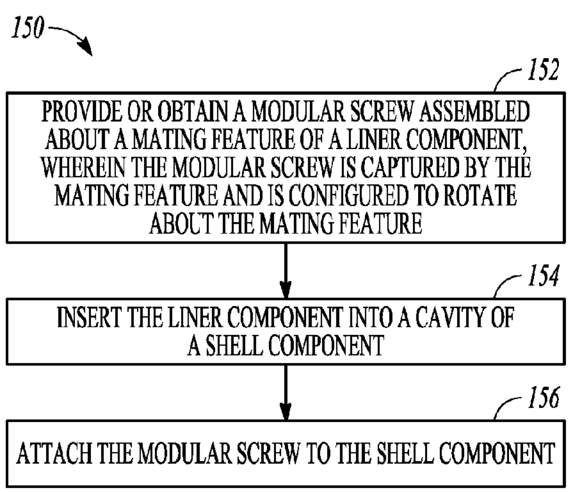
FIG. 6 is a flow chart illustrating an example of a method of assembling a modular screw apparatus to a liner component.

FIG. 6 is a flow chart illustrating an example of a method 150 of assembling a modular screw to a liner component and a shell component. At 152, the modular screw can be provided or obtained assembled about a mating feature of the liner component. The modular screw can be captured by the mating feature while retaining the ability to rotate about the mating feature. The modular screw can be assembled by any suitable means, including press or snap fitting a male component into a female component. In an example, the mating feature can include a groove that can be configured to receive a protrusion extending from the male component to prevent lateral movement of the modular screw during rotation of the screw. The male and female components can be fused or otherwise joined together, such as by electron beam welding, so that the components are affixed.

At 154, the liner component can be inserted into a cavity of the shell component, such that the liner component can abduct or adduct about an axis of symmetry of the shell component.

At 156, the modular screw can be attached to the shell component, so as to form an articulate assembly. The modular screw can be threaded to the shell component with a torque device, such as those described herein.

Trial reduction of the shell component and liner component can be conducted, so as to assess stability of the shell component within a cup-shaped site or to assess the range of motion of one or more components coupled to the shell component or the liner component. Off-axis forces can occur as a result of trial reduction, such that strain can be placed on the modular screw. The modular screw can include affixed male and female components such that off-axis forces can be withstood by the modular screw without experiencing component material fatigue, detachment of the modular screw from the shell component, or decapturing of the mating feature by the female and male modular screw components.

In an example, bone quality of the cup-shaped site of a subject can be determined, such as by visual inspection or medical imaging. A shell component can be selected according to a size of the cup-shaped site. A shell component inserter can be used to insert the shell component into the cup-shaped site. A liner component can be selected that corresponds to the size of the selected shell component. For example, the shell component and the liner component can be a pair, such that the liner component can fit within a cavity of the shell component.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed:

1. An implantable acetabular assembly, comprising:

a cup-shaped shell configured to be inserted into a cup-shaped site;

a cup-shaped liner configured to be received within a cavity of the shell, the liner having a liner aperture and a mating feature adjacent to the aperture; and a modular screw configured to be received within the aperture of the liner, the modular screw including a first component that is positionable adjacent to a first side of the mating feature and a second component that is positionable adjacent to a second side of the mating feature opposite the first side, wherein the modular screw is configured to be rotatable within the aperture of the liner when the first component and second component are coupled to each other;

wherein the first component of the modular screw is a female component having an externally threaded portion configured to be engaged with mating internal threads in a shell aperture of the shell, wherein the second component of the modular screw is a male component configured to be received within a recess in the female component so as to couple the modular screw about the mating feature, and wherein the male component includes a cavity to receive a torque driver to rotate the modular screw, wherein rotation of the male component rotates the female component to threadingly engage the internal threads in the shell aperture, and wherein the male component is coupled to the female component with at least one of a press fit connection and a snap fit connection.

2. The implantable acetabular assembly of claim 1, wherein the male component is fused to the female component to prevent separation of the male and female components.

3. The implantable acetabular assembly of claim 2, wherein the male component and the female component are fused together using electron beam welding.

4. The implantable acetabular assembly of claim 1, wherein the male component includes a head having the cavity configured to receive the torque driver for attaching the modular screw to the shell.

5. The implantable acetabular assembly of claim 4, wherein the cavity includes a depth configured to permit a threshold torque for attaching the threaded portion of the female component to the shell.

6. The implantable acetabular assembly of claim 4, wherein the mating feature is a radially extending flange.

7. The implantable acetabular assembly of claim 6, wherein the radially extending flange is configured to withstand off-axis leveraging of the modular screw.

8. The implantable acetabular assembly of claim 6, wherein the female component includes a female seating surface configured to be positioned adjacent to the first side of the radially extending flange.

9. The implantable acetabular assembly of claim 6, wherein the head of the male component includes a male seating surface configured to be positioned adjacent to the second side of the radially extending flange.

10. The implantable acetabular assembly of claim 9, wherein the second side includes a groove configured to receive a protrusion on the male seating surface for rotation of the modular screw relative to the liner.

11. The implantable acetabular assembly of claim 9, wherein a lateral dimension of the radially extending flange is greater than a lateral dimension of the seating surfaces of the female and male components.

12. The implantable acetabular assembly of claim 1, wherein:

the first component of the modular screw includes a first flange configured to be positioned adjacent to the first side of the mating feature; and the second component includes a second flange configured to be positioned adjacent to the second side of the mating feature.

* * * * *